(12) United States Patent
Shin et al.

(10) Patent No.: US 7,847,039 B2
(45) Date of Patent: Dec. 7, 2010

(54) TRANSITION METAL COMPLEXES, AND CATALYSTS COMPOSITIONS FOR PREPARING ETHYLENE HOMOPOLYMERS OR COPOLYMERS

(75) Inventors: Dong-Cheol Shin, Daejeon (KR); Ho-Seong Lee, Seoul (KR); Myung-Ahn Ok, Daejeon (KR); Jong-Sok Hahn, Daejeon (KR)

(73) Assignee: SK Energy Co., Ltd., Seoul (KR)

( * ) Notice: Subject to any disclaimer, the term of this patent is extended or adjusted under 35 U.S.C. 154(b) by 146 days.

(21) Appl. No.: 12/318,672

(22) Filed: Jan. 6, 2009

(65) Prior Publication Data

US 2009/0176948 A1    Jul. 9, 2009

(30) Foreign Application Priority Data

Jan. 7, 2008    (KR) .................. 10-2008-0001647

(51) Int. Cl.
C08F 4/76 (2006.01)
C08F 4/52 (2006.01)
C08F 4/64 (2006.01)

(52) U.S. Cl. .................. 526/161; 526/172; 526/160; 526/170; 526/134; 526/348; 526/73; 502/103; 556/51; 556/52

(58) Field of Classification Search .................. 556/51, 556/52; 526/172, 161
See application file for complete search history.

(56) References Cited

U.S. PATENT DOCUMENTS

| | | | |
|---|---|---|---|
| 4,752,597 A | 6/1988 | Turner | |
| 5,079,205 A | 1/1992 | Canich | |
| 5,198,401 A | 3/1993 | Turner et al. | |
| 6,329,478 B1 | 12/2001 | Katayama et al. | |
| 6,967,231 B1 | 11/2005 | Wang et al. | |
| 7,589,042 B2 * | 9/2009 | Woo et al. | 502/152 |
| 7,645,715 B2 * | 1/2010 | Ok et al. | 502/152 |

FOREIGN PATENT DOCUMENTS

| | | |
|---|---|---|
| EP | 0 320 762 | 6/1989 |
| EP | 0 372 632 | 6/1990 |
| EP | 0 416 815 | 3/1991 |
| EP | 0 420 436 | 4/1991 |
| EP | 0 842 939 | 5/1998 |
| EP | 1013675 B1 | 7/2002 |
| EP | 1195386 B1 | 6/2007 |
| JP | 63-92621 | 4/1988 |
| JP | 2-84405 | 3/1990 |
| JP | 3-2347 | 1/1991 |
| KR | 10-2001-0074722 | 8/2001 |

OTHER PUBLICATIONS

Inoue et al., Chemistry Letters, 2001, 1060-1061.*
K. Nomura et al., "Synthesis of Various Nonbridged Titanium(IV) Cyclopentadienyl-Aryloxy Complexes of the Type CpTi(OAr)$X_2$ and Their Use in the Catalysis of Alkene Polymerization. Important Roles of Substituents on both Aryloxy and Cyclopentadienyl Groups", *Organometallics* 1998, 17, 2152-2154.
J. Randall, "A Review of High Resolution Liquid [13]Carbon Nuclear Magnetic Resonance Characterizations of Ethylene-Based Polymers", *JMS-REV. Macromol. Chem. Phys.* C29(2&3), 201-317 (1989).
K. Nomura et al., "Nonbridged half-metallocenes containing anionic ancillary donor ligands: New promising candidates as catalysts for precise olefin polymerization" *Journal of Molecular Catalysis A: Chemical* 267 (2007) 1-29.

* cited by examiner

*Primary Examiner*—Rip A. Lee
(74) *Attorney, Agent, or Firm*—Clark & Brody

(57) ABSTRACT

Disclosed are a transition metal complex having a high catalytic activity for the preparation of an ethylene homopolymer or a copolymer of ethylene and α-olefin and a catalyst composition comprising the same. More specifically, there are provided a transition metal complex having, around a group IV transition metal, a cyclopentadiene derivative and at least one aryl oxide ligand with a heterocyclic aryl derivative substituted at the ortho-position thereof, with no crosslinkage between the ligands, a catalyst composition comprising the transition metal complex and an organoaluminum compound or boron compound as cocatalyst, and a method for the preparation of high molecular weight ethylene homopolymers or copolymers of ethylene and α-olefin using the same.

16 Claims, No Drawings

TRANSITION METAL COMPLEXES, AND CATALYSTS COMPOSITIONS FOR PREPARING ETHYLENE HOMOPOLYMERS OR COPOLYMERS

TECHNICAL FIELD

The present invention relates to a transition metal catalyst system for the preparation of an ethylene homopolymer or a copolymer of ethylene and α-olefin, more particularly to: a group IV transition metal complex having, around a group IV transition metal, a cyclopentadiene derivative and at least one aryl oxide ligand with a heterocyclic aryl derivative substituted at the ortho-position thereof, with no crosslinkage between the ligands; a transition metal catalyst composition for the preparation of an ethylene homopolymer or a copolymer of ethylene and α-olefin comprising the transition metal complex, a boron compound cocatalyst and an aluminum compound cocatalyst; and a method for the preparation of an ethylene homopolymer or a copolymer of ethylene and α-olefin using the catalyst composition.

BACKGROUND ART

Conventionally, a Ziegler-Natta catalyst system consisting of a titanium or vanadium compound as main catalyst component and an alkylaluminum compound as cocatalyst component has been used for the preparation of ethylene homopolymers or copolymers thereof with α-olefin. Although the Ziegler-Natta catalyst system is highly active in the polymerization of ethylene, it has heterogeneous catalytic active sites, leading to a polymer having a broad molecular weight distribution and, and in particular, a copolymer of ethylene and α-olefin having a non-uniform compositional distribution.

Recently, the so-called metallocene catalyst system has been developed, which consists of a metallocene compound of a group IV transition metal such as titanium, zirconium, hafnium, etc. and a methylaluminoxane cocatalyst. Since the metallocene catalyst system is a homogeneous catalyst having homogeneous catalytic active sites, it can provide a narrower molecular weight distribution than the Ziegler-Natta catalyst system and can be used to prepare polyethylene having uniform compositional distribution. For example, European Patent Publication Nos. 320,762 and 372,632 and Japanese Patent Laid-open Nos. Sho 63-092621, Hei 02-084405 and Hei 03-002347 disclose metallocene compounds such as $Cp_2TiCl_2$, $Cp_2ZrCl_2$, $Cp_2ZrMeCl$, $Cp_2ZrMe_2$, ethylene $(IndH_4)_2ZrCl_2$, activated with methylaluminoxane as a cocatalyst to polymerize ethylene at high catalytic activity, thereby making it possible to produce polyethylene having a molecular weight distribution ($M_w/M_n$) of 1.5-2.0. However, it is difficult to obtain polymers having high molecular weights using the catalyst system. Further, in the case where such a catalyst system is applied to solution polymerization at high temperatures of 140° C. or above, polymerization activity is drastically decreased, and β-dehydrogenation predominates, and thus the catalyst system is known to be unsuitable for the production of high molecular weight polymers having a weight average molecular weight ($M_w$) of 100,000 or more.

In addition, the so-called non-metallocene catalyst having a geometrically constrained structure (also known as single active site catalyst) has been presented, in which a transition metal is linked to form a ring, as a catalyst for the preparation of high molecular weight ethylene homopolymers or copolymers of ethylene and α-olefin by solution polymerization with high catalytic activity. European Patent Publication Nos. 0416815 and 0420436 disclose a catalyst having a geometrically constrained structure in which an amide group is linked to a single cyclopentadiene ligand to form the shape of a ring. European Patent Publication No. 0842939 discloses a catalyst in which a phenolic ligand as an electron donating compound is linked to a cyclopentadiene ligand to form a ring. However, such geometrically constrained catalysts are commercially inapplicable because the yield of ring formation between the ligand and the transition metal compound during the catalyst synthesis is very low.

Further, non-metallocene catalysts without having a geometrically constrained structure but applicable in high temperature solution conditions are disclosed in U.S. Pat. No. 6,329,478 and Korean Patent Publication No. 2001-0074722. In these patents, single active site catalysts having at least one phosphinimine compound as ligand are used to provide high ethylene transition ratio in copolymerization of ethylene and α-olefin under high temperature solution polymerization condition of 140° C. or higher. However, they required the use of a phosphine compound for the synthesis of the phosphinimine ligand. Because the compound is harmful to the environment and humans, the catalysts are inapplicable to the production of general-use olefin polymers. U.S. Pat. No. 5,079,205 discloses a catalyst having a bis(phenoxide) ligand, but the catalytic activity is too low to be commercially applicable.

In addition, a non-metallocene catalyst having a phenolic ligand and its application for polymerization are disclosed in *Organometallics* 1998, 17, 2152 (Nomura et al.). However, the alkyl substituent is restricted to an isopropyl group.

DISCLOSURE

Technical Problem

The inventors of the present invention have carried out researches extensively in order to overcome the aforesaid problems of the existing technologies. As a result, they have found out that a non-crosslinked transition metal catalyst having a cyclopentadiene derivative and an aryl oxide ligand with a heterocyclic aryl derivative substituted at the ortho-position thereof provides superior catalytic activity in polymerization of ethylene. Based on this finding, they have developed a catalyst capable of producing high molecular weight olefin homopolymers or copolymers through olefin polymerization carried out at 60° C. or above, and completed the present invention.

Accordingly, the present invention is directed to provide a transition metal complex having a non-crosslinked structure, being very economical and providing excellent catalytic activity in olefin polymerization, and a transition metal catalyst composition for the preparation of an ethylene homopolymer or a copolymer of ethylene and α-olefin comprising the transition metal complex and a cocatalyst. The invention is also directed to provide a method for the polymerization of ethylene homopolymers or copolymers of ethylene and α-olefin having various physical properties using the transition metal complex and the catalyst composition, which can be prepared economically in a commercial point or view.

Technical Solution

In an aspect, the present invention provides a transition metal complex represented by the following Chemical Formula 1, which has, around a group IV transition metal, a cyclopentadiene derivative and at least one aryl oxide ligand with a heterocyclic aryl derivative substituted at the ortho-position thereof, with no crosslinkage between the ligands:

[Chemical Formula 1]

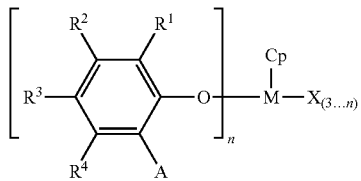

wherein

M is a group IV transition metal in the periodic table;

Cp is a cyclopentadienyl ring or a fused ring including a cyclopentadienyl ring, which is able to be $\eta^5$-bonded to the central metal M, wherein the cyclopentadienyl ring or cyclopentadienyl fused ring may be further substituted with (C1-C20) alkyl, (C6-C30) aryl, (C2-C20) alkenyl or (C6-C30) aryl (C1-C20) alkyl;

A is a substituent

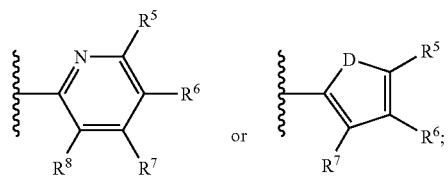

$R^1, R^2, R^3, R^4, R^5, R^6, R^7$ and $R^8$ are, independently of each other, hydrogen, (C1-C20) alkyl, (C3-C20) cycloalkyl, (C1-C20) alkyl-substituted or (C6-C30) aryl-substituted silyl, (C6-C30) aryl, (C6-C30) aryl (C1-C20) alkyl, (C1-C20) alkoxy, (C1-C20) alkyl-substituted or (C6-C30) aryl-substituted siloxy, (C1-C20) alkyl-substituted or (C6-C30) aryl-substituted amino, (C1-C20) alkyl-substituted or (C6-C30) aryl-substituted phosphino, (C1-C20) alkyl-substituted mercapto or nitro, wherein the alkyl, aryl or alkoxy group of said $R^1$ to $R^8$ may be further substituted with halogen or may form a fused ring together with a neighboring substituent;

D is N—$R^9$, oxygen or sulfur;

$R^9$ is linear or branched (C1-C20) alkyl, (C6-C30) aryl, (C1-C20) alkyl-substituted or (C6-C30) aryl-substituted silyl;

n is an integer 1 or 2; and

X is, independently of each other, halogen, (C1-C20) alkyl, (C3-C20) cycloalkyl, (C6-C30) aryl (C1-C20) alkyl, (C1-C20) alkoxy, (C3-C20) alkylsiloxy, (C1-C20) alkyl-substituted or (C6-C30) aryl-substituted amino, (C1-C20) alkyl-substituted or (C6-C30) aryl-substituted phosphino or (C1-C20) alkyl-substituted mercapto.

In another aspect, the present invention provides a catalyst composition for the preparation of an ethylene homopolymer or a copolymer of ethylene and α-olefin comprising said transition metal complex, and a boron compound or an aluminum compound as cocatalyst.

In another aspect, the present invention provides a method for the preparation of an ethylene homopolymer or a copolymer of ethylene and α-olefin using said transition metal complex or transition metal catalyst composition, and an ethylene homopolymer or a copolymer of ethylene and α-olefin prepared thereby.

Hereinafter, the present invention is described in more detail.

In the transition metal complex of Chemical Formula 1, the central metal M may be titanium, zirconium or hafnium. Cp include a cyclopentadiene anion or a cyclopentadienyl ring which is able to be $\eta^5$-bonded to the central metal M. Specific examples of substitution or non-substitution a fused ring derivative may include cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, isopropylfluorenyl, etc.

A may be a substituent

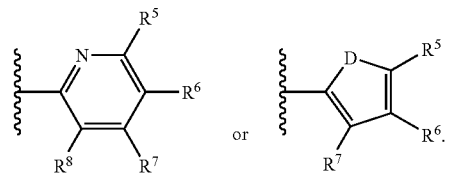

Specific examples may include the compounds represented by the following Chemical Formula 2 and Chemical Formula 3:

[Chemical Formula 2]

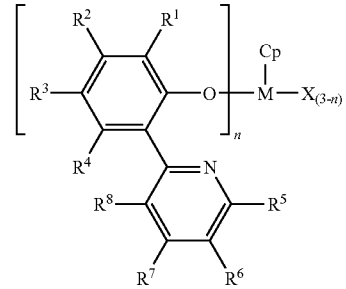

[Chemical Formula 3]

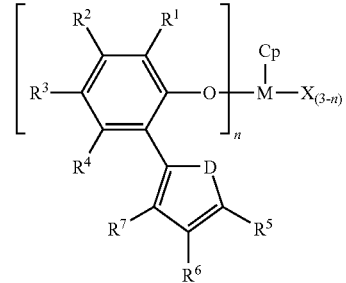

In Chemical Formulas I-3, the substituents $R^1, R^2, R^3, R^4, R^5, R^6, R^7$ and $R^8$ in the heterocyclic aryl-substituted aryl oxide ligand may be: halogen, e.g., fluorine, chlorine, bromine or iodine; linear or non-linear (C1-C20) alkyl e.g., methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl or tert-butyl; (C3-C20) cycloalkyl, e.g., cyclopropyl, cyclobutyl, cyclopentyl, cyclohexyl, cycloheptyl or adamantyl, preferably cyclopentyl or cyclohexyl; (C1-C20) alkyl-substituted or (C6-C30) aryl-substituted silyl, e.g., methylsilyl, ethylsilyl, phenylsilyl, dimethylethylsilyl, diethylmethylsilyl, diphenylmethylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyldimethylsilyl, tri-n-pentylsilyl, tri-n-hexylsilyl, tricyclohexylsilyl or triphenylsilyl, preferably trimethylsilyl, tert-butyldimethylsilyl or triphenylsilyl; (C6-C30) aryl or (C1-C20) alkyl (C6-C30) aryl, e.g., phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl or anthracenyl, preferably phenyl, naphthyl, biphenyl, 2-isopropylphenyl, 3,5-xylyl or 2,4,6-trimethylphenyl; (C6-C30) aryl (C1-C10) alkyl, e.g., benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trim ethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, triphenylmethyl, naphthylmethyl or anthracenylmethyl, preferably benzyl or triphenylmethyl; (C1-C20) alkoxy, e.g. methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; (C1-C20) alkyl-substituted or (C6-C20) aryl-substituted siloxy, e.g., trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy or tricyclohexylsiloxy, preferably trimethylsiloxy or tert-butyldimethylsiloxy; (C1-C20) alkyl-substituted or (C6-C30) aryl-substituted amino, e.g., dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino, or corresponding alkyl-substituted phosphino, preferably dimethylamino, diethylamino or diphenylamino; or (C1-C20) alkyl-substituted or (C6-C30) aryl-substituted phosphine, e.g., dimethylphosphino, diethylphosphino, di-n-propylphosphino, diisopropylphosphino, di-n-butylphosphino, di-sec-butylphosphino, di-tert-butylphosphino, diisobutylphosphino, tert-butylisopropylphosphino, di-n-hexylphosphino, di-n-octylphosphino, di-n-decylphosphino, diphenylphosphino, dibenzylphosphino, methylethylphosphino, methylphenylphosphino, benzylhexylphosphino, bistrimethylsilylphosphino or bis-tert-butyldimethylsilylphosphino, preferably dimethylphosphino, diethylphosphino or diphenylphosphino; (C1-C20) alkyl-substituted mercapto, e.g., methylmercapto, ethylmercapto, propylmercapto, isopropylmercapto, 1-butylmercapto or isopentylmercapto, preferably ethylmercapto, or isopropylmercapto; and the alkyl, aryl or alkoxy group of said $R^1$ to $R^8$ may be further substituted with halogen or may form a fused ring with a neighboring substituent.

$R^9$ may be: linear or non-linear (C1-C20) alkyl, e.g., methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl, tert-butyl or amyl; or (C1-C20) alkyl-substituted or (C6-C30) aryl-substituted silyl, e.g., methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyidimethylsilyl, tri-n-pentylsilyl, tri-n-hexylsilyl, tricyclohexylsilyl or triphenylsilyl, preferably trimethylsilyl, tert-butyldimethylsilyl or triphenylsilyl.

X may be: halogen, e.g., fluorine, chlorine, bromine or iodine; (C1-C20) alkyl which is not a Cp derivative, e.g., methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl or n-eicosyl, preferably methyl, ethyl, isopropyl, tert-butyl or amyl; (C3-C20) cycloalkyl, e.g., cyclopropyl, cyclobutyl, cyclopentyl, cyclohexyl, cycloheptyl or adamantyl, preferably cyclopentyl or cyclohexyl; (C6-C30) aryl (C1-C20) alkyl, e.g., benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl or anthracenylmethyl, preferably benzyl; (C1-C20) alkoxy, e.g., methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy or n-eicosoxy, preferably methoxy, ethoxy, isopropoxy or tert-butoxy; (C3-C20) alkylsiloxy, e.g., trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyidimethylsilyl, tri-n-pentylsiloxy, tri-n-hexylsiloxy or tricyclohexylsiloxy, preferably trimethylsiloxy or tert-butyldimethylsiloxy; (C1-C20) alkyl-substituted or (C6-C30) aryl-substituted amino, or (C1-C20) alkyl-substituted or (C6-C30) aryl-substituted phosphine, e.g., dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino or bis-tert-butyldimethylsilylamino, or corresponding alkyl-substituted phosphino, preferably dimethylamino, diethylamino or diphenylamino; or (C1-C20) alkyl-substituted mercapto, e.g., methylmercapto, ethylmercapto, propylmercapto, isopropylmercapto, 1-butylmercapto or isopentylmercapto.

For olefin polymerization, the transition metal complex of Chemical Formula 1 may be used with a boron compound, organoaluminum compound or a mixture thereof, which can function as a counterion, i.e. anion, capable of withdrawing the ligand X from the transition metal complex and cationizing the central metal, and having weak binding capacity, as cocatalyst. The organoaluminum compound may serve to remove trace polar materials acting as catalytic poison, e.g., water. However, in case the ligand X is halogen, it may act as an alkylating agent.

The boron compound that can be used in the present invention as cocatalyst may be selected from the compounds represented by the followings Chemical Formulas 4 to 6, which are disclosed in U.S. Pat. No. 5,198,401:

$B(R^{10})_3$ [Chemical Formula 4]

$[R^{11}]^+[B(R^{10})_4]^-$ [Chemical Formula 5]

$[(R^{12})_q ZH]^+[B(R^{10})_4]^-$ [Chemical Formula 6]

Wherein chemical formulas 4-6,
B is boron;
$R^{10}$ is phenyl, which may be further substituted with 3 to 5 substituents selected from fluorine, fluorine-substituted or unsubstituted (C1-C20) alkyl and fluorine-substituted or unsubstituted (C1-C20) alkoxy;
$R^{11}$ is (C5-C7) aromatic radical, (C1-C20) alkyl (C6-C20) aryl radical or (C6-C30) aryl (C1-C20) alkyl radical, e.g., triphenylmethyl radical;
Z is nitrogen or phosphorus;
$R^{12}$ is (C1-C20) alkyl radical or anilinium radical substituted with nitrogen and two (C1-C10) alkyls; and
q is an integer 2 or 3.

Preferred examples of the boron-based cocatalyst may include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-tetrafluorophenyl)borate, tetrakis(2,2,4-trifluorophenyl)borate, phenylbis(pentafluorophenyl)borate or tetrakis(3,5-bistrifluoromethylphenyl)borate. Further, ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate or tri(dimethylphenyl)phosphonium tetrakis(pentafluorophenyl)borate, preferably N,N-dimethylinium tetrakis(pentafluorophenyl)borate, triphenylmethylinium tetrakis(pentafluorophenyl)borate or trispentafluoroborane may be used.

The aluminum compound used in the present invention may be an aluminoxane compound represented by the following Chemical Formula 7 or Chemical Formula 8, an organoaluminum compound represented by the following Chemical Formula 9, or an organoaluminum hydrocarbyl oxide compound represented by the following Chemical Formula 10 or Chemical Formula 11:

$(-Al(R^{13})-O-)_m$ [Chemical Formula 7]

$(R^{13})_2 Al-(-O(R^{13})-)_p-(R^{13})_2$ [Chemical Formula 8]

$(R^{14})_r Al(E)_{3-r}$ [Chemical Formula 9]

$(R^{15})_2 AlOR^{16}$ [Chemical Formula 10]

$R^{15} Al(OR^{16})_2$ [Chemical Formula 11]

Wherein chemical formula 7-11
$R^{13}$ is (C1-C20) alkyl, preferably methyl or isobutyl;
m and p are integers from 5 to 20;
$R^{14}$ and $R^{15}$ are (C1-C20) alkyl;
E is hydrogen or halogen;
r is an integer from 1 to 3; and
$R^{16}$ is (C1-C20) alkyl or (C6-C30) aryl.

Specific examples of the aluminum compound may include: an aluminoxane compound such as methylaluminoxane, modified methylaluminoxane and tetraisobutylaluminoxane; an organoaluminum compound such as trialkylaluminum dimethylaluminum chloride including trimethylaluminum, triethylaluminum, tripropylaluminum, triisobutylaluminum and trihexylaluminum, dialkylaluminum chloride methylaluminum dichloride including diethylaluminum chloride, dipropylaluminum chloride, diisobutylaluminum chloride and dihexylaluminum chloride, alkylaluminum dichloride dimethylaluminum hydride including ethylaluminum dichloride, propylaluminum dichloride, isobutylaluminum dichloride and hexylaluminum dichloride, and dialkylaluminum hydride including diethylaluminum hydride, dipropylaluminum hydride, diisobutylaluminum hydride and dihexylaluminum hydride, preferably trialkylaluminum, and more preferably triethylaluminum and triisobutylaluminum.

The molar ratio of the central transition metal M:boron atom:aluminum atom may be preferably 1:0.1-100:10-1,000, more preferably 1:0.5-5:25-500.

A method for the preparation of olefin polymers using the transition metal or the catalyst composition comprising the transition metal according to the present invention is performed by contacting the transition metal catalyst, the cocatalyst and ethylene and, optionally, a vinylic comonomer in the presence of an adequate organic solvent. The transition metal catalyst and the cocatalyst components may be provided separately to a reactor. Alternatively, they may be mixed in advance before adding to the reactor. Mixing conditions, including the sequence of addition, temperature, concentration, or the like, are not particularly limited.

Preferably, the organic solvent may be (C3-C20) hydrocarbon. Specific examples may include butane, isobutane, pentane, hexane, heptane, octane, isooctane, nonane, decane, dodecane, cyclohexane, methylcyclohexane, benzene, toluene, xylene, and the like.

Specifically, when preparing the ethylene homopolymer high-density polyethylene (HDPE), ethylene is used as monomer alone. Pressure of ethylene may be 1-1,000 atm, more preferably 8-150 atm. And, polymerization temperature may be 60-300° C., preferably 80-250° C.

When preparing a copolymer of ethylene and α-olefin, (C3-C18) α-olefin may be used as comonomer in addition to ethylene. Preferably, it may be selected from a group consisting of propylene, 1-butene, 1-pentene, 4-methyl-1-pentene, 1-hexene, 1-octene, 1-decene, 1-dodecene, 1-hexadecene and 1-octadecene. More preferably, propylene, 1-butene, 1-hexene, 1-octene or 1-decene may be copolymerized with ethylene. Preferred pressure of ethylene and polymerization temperature are the same as in the preparation of HDPE described above. Typically, thus prepared ethylene copolymer has an ethylene content of 50% by weight or more, preferably 60% by weight or more, more preferably 60-99% by weight.

Linear low-density polyethylene (LLDPE) prepared using (C4-C10) α-olefin as comonomer may have a density ranging from 0.910 to 0.940 g/cc. Further, very low-density polyethylene (VLDPE), ultra low-density polyethylene (ULDPE) or olefin elastomer having a density smaller than 0.910 g/cc may be obtained. During the preparation of an ethylene homopolymer or copolymer, hydrogen may be added to control molecular weight. Typically, the resultant polymer has a weight average molecular weight ($M_w$) ranging from 80,000 to 500,000.

Since the transition metal or the catalyst composition comprising the transition metal according to the present invention exists in a homogeneous state in the polymerization reactor, it may be preferably applied to a solution polymerization process performed at a temperature above the melting point of the corresponding polymer. However, as disclosed in U.S. Pat. No. 4,752,597, the transition metal catalyst and the cocatalyst may be supported on a porous metal oxide support for application to a slurry polymerization or vapor-phase polymerization process as a heterogeneous catalyst system.

ADVANTAGEOUS EFFECTS

The transition metal complex having an arylphenoxy ligand and the catalyst composition comprising the transition metal complex according to the present invention are easy to handle, can be prepared in high yield using environment-friendly source materials, and can be used to produce high molecular weight polymers under high-temperature solution polymerization condition because of excellent thermal stability and superior catalytic activity at high temperature. Therefore, they are more practical than previously known non-metallocene single active site catalysts, and can be utilized usefully to prepare ethylene homopolymers or copolymers of ethylene and α-olefin having various physical properties.

MODE FOR INVENTION

Hereinafter, the present invention will be described in more detail through examples. However, the following examples are not intended to limit the scope of the present invention.

Unless specified otherwise, all ligand and catalyst syntheses were carried out under nitrogen atmosphere using standard Schlenk or glovebox techniques. Organic solvents were subjected to reflux in the presence of sodium metal and benzophenone to remove moisture, followed by distillation, prior to use. Synthesized ligands and catalysts were subjected to $^1$H-NMR analysis at room temperature, using Varian Oxford 300 MHz.

The polymerization solvent n-heptane was passed through a column packed with molecular sieve 5A and activated alumina, and purged with high-purity nitrogen in order to sufficiently remove water, oxygen or any other catalytic poisons. Polymerized polymers were analyzed as described below.

1. Melt index (MI)
Measured in accordance with ASTM D 2839.
2. Density
Measured in accordance with ASTM D 1505 using a density gradient column.
3. Melting point ($T_m$)
Measured using Dupont DSC2910 under nitrogen atmosphere under 2nd heating condition at a rate of 10° C./min.
4. Molecular weight and molecular weight distribution
Measured using PL210 GPC equipped with PL Mixed-BX2+preCol at 135° C., at a speed of 1.0 mL/min in the presence of a 1,2,3-trichlorobenzene solvent. The molecular weight was corrected using PL polystyrene standard material.
5. α-Olefin content (% by weight)
Measured using Bruker DRX500 NMR spectrometer at 125 MHz, using a 1,2,4-trichlorobenzene/$C_6D_6$ (7/3 based on weight) mixture solvent at 120° C. in $^{13}$C-NMR mode [see Randal, J. C. *JMS-Rev. Macromol. Chem. Phys.* 1980, C29, 201].

Preparation Example 1

Synthesis of (dichloro)(pentamethylcyclopentadienyl)(2-(thiophen-2'-yl)phenoxy)titanium(IV)

Synthesis of 2-(2'-methoxyphenyl)thiophene

2-Bromothiophene (7.2 g, 43.9 mmol), 2-methoxyphenylboronic acid (6.7 g, 43.9 mmol), palladium acetate (0.14 g, 0.62 mmol), triphenylphosphine (0.6 mg, 2.3 mmol) and potassium phosphate (9.40 g, 44.3 mmol) were added to a flask. A mixture solution of 10 mL of water and 40 mL of dimethoxyethane was added and reflux was performed for 6 hours. After cooling to room temperature, aqueous ammonium chloride solution (50 mL) and diethyl ether (100 mL) were added. The organic layer was separated. After extracting the residue using diethyl ether, the collected organic layer was dried with magnesium sulfate. After removing volatile materials, followed by purification via silica gel chromatography using hexane, 7.9 g (yield: 95%) of 2-(2'-methoxyphenyl)thiophene was obtained as colorless liquid.

$^1$H-NMR ($C_6D_6$) δ=3.26 (s, 3H), 6.49-6.53 (d, 1H), 6.77-7.03 (m, 4H), 7.47-7.49 (d, 1H), 7.60-7.64 (d, 1H) ppm Synthesis of 2-(thiophen-2'-yl)phenol 2-(2'-Methoxyphenyl)thiophene (7 g, 36.8 mmol) was dissolved in 100 mL of methylene chloride. At −78° C., 40 mL of boron tribromide (1 M methylene chloride solution) was added dropwise. Reaction was carried out for 3 hours while slowly heating to room temperature. Then, a mixture solution of ice (50 g) and diethyl ether (100 mL) was added. The organic layer was separated. After extracting the aqueous layer using diethyl ether, the collected organic layer was dried with magnesium sulfate. After removing volatile materials, followed by purification via silica gel chromatography using a mixture solution of hexane and methylene chloride, 2.9 g (yield: 40%) of 2-(thiophen-2'-yl)phenol was obtained as colorless liquid.

$^1$H-NMR ($C_6D_6$) δ=6.54-6.58 (d, 1H), 6.59-6.95 (m, 4H), 7.12-7.15 (d, 1H), 7.36-7.41 (d, 1H) ppm Synthesis of (dichloro)(pentamethylcyclopentadienyl)(2-(thiophen-2'-yl)phenoxy)titanium(IV)

2-(Thiophen-2'-yl)phenol (2.07 g, 11.76 mmol, Aldrich) was added to a dry flask. After dissolving with diethyl ether, the temperature was lowered to 0° C. while stirring well. n-Butyllithium (8.08 mL, 1.6 M in hexane, Aldrich) was slowly added dropwise to the mixture. Then, after maintaining the temperature for 1 hour, the temperature was raised to room temperature and stirring was carried out for 12 hours.

After removing the solvent layer, the precipitate was washed with hexane. After removing volatile materials, the precipitate was dissolved in toluene. This mixture was cooled to 0° C. and pentamethylcyclopentadienyltitanium chloride (1.70 g, 5.88 mmol) dissolved in toluene was slowly added dropwise. After maintaining the temperature for 1 hour, the temperature was raised to room temperature and stirring was carried out for 24 hours. Then, the solid material was removed by filtering. After removing volatile materials again from the resultant solution, recrystallization was carried out in toluene. 1.64 g (yield: 65%) of orange crystal was obtained.

$^1$H-NMR (C$_6$D$_6$) δ=1.73 (s, 15H), 6.75-6.79 (d, 1H), 6.85-6.94 (m, 3H), 7.14-7.18 (d, 1H), 7.41-7.45 (d, 1H)), 7.57-7.59 (d, 1H) ppm Mass (APCl mode, m/z): 429

Preparation Example 2

Synthesis of (dichloro)(pentamethylcyclopentadienyl)(2-(pyridin-2'-yl)phenoxy)titanium(IV)

Synthesis of 2-(2'-methoxyphenyl)pyridine

2-Bromopyridine (4.28 mL, 43.9 mmol), 2-methoxyphenylboronic acid (6.7 g, 43.9 mmol), palladium acetate (0.14 g, 0.62 mmol), triphenylphosphine (0.6 mg, 2.3 mmol) and potassium phosphate (9.40 g, 44.3 mmol) were added to a flask. A mixture solution of 10 mL of water and 40 mL of dimethoxyethane was added and reflux was performed for 6 hours. After cooling to room temperature, aqueous ammonium chloride solution (50 mL) and diethyl ether (100 mL) were added. The organic layer was separated. After extracting the residue using diethyl ether, the collected organic layer was dried with magnesium sulfate. After removing volatile materials, followed by purification via silica gel chromatography using n-hexane, 7.7 g (yield: 95%) of 2-(2'-methoxyphenyl)pyridine was obtained as colorless liquid.

$^1$H-NMR (C$_6$D$_6$) δ=3.22 (s, 3H), 6.55-8.67 (m, 8H) ppm

Synthesis of 2-(pyridin-2'-yl)phenol 40 mL of pyridine was added to 40 mL of 35% hydrochloric acid. After stirring at 200° C. for 30 minutes, followed by removing water by distillation at 220° C., 2-(2'-methoxyphenyl)pyridine (6.8 g, 36.8 mmol) was added and reaction was carried out at 200° C. for 12 hours. After cooling to room temperature, followed by addition of distilled water, titration was carried out using aqueous sodium hydroxide solution. After extracting the organic layer using methylene chloride, followed by drying with magnesium sulfate, volatile materials were removed and purification was carried out via silica gel chromatography using a mixture solution of hexane and ethyl acetate. 3.5 g (yield: 52%) of 2-(pyridin-2'-yl)phenol was obtained as yellow solid.

$^1$H-NMR (C$_6$D$_6$) δ=6.30-7.72 (m, 7H), 8.43-8.67 (m, 2H) ppm

Synthesis of (dichloro)(pentamethylcyclopentadienyl)(2-(pyridin-2'-yl)phenoxy)titanium(IV)

2-(Pyridin-2'-yl)phenol (2.64 g, 15.42 mmol, Aldrich) was added to a dry flask. After dissolving with toluene, the temperature was lowered to 0° C. while stirring well. n-Butyllithium (5.86 mL, 2.5 M in hexane, Aldrich) was slowly added dropwise to the mixture. Then, after maintaining the temperature for 1 hour, the temperature was raised to room temperature and stirring was carried out for 12 hours. After removing the solvent layer, the precipitate was washed with purified n-hexane. After removing volatile materials, the precipitate was dissolved in toluene. This mixture was cooled to 0° C. and pentamethylcyclopentadienyltitanium chloride (2.23 g, 12.59 mmol) dissolved in toluene was slowly added dropwise. After maintaining the temperature for 1 hour, the temperature was raised to room temperature and stirring was carried out for 24 hours. Then, the solid material was removed by filtering. After removing volatile materials again from the resultant solution, recrystallization was carried out in toluene. 2.1 g (yield: 49%) of orange crystal was obtained.

$^1$H-NMR (C$_6$D$_6$) δ=1.66 (s, 15H), 6.61-7.35 (m, 5H), 7.80 (m, 1H), 8.08 (m, 1H), 8.62 (m, 1H) ppm Mass (APCl mode, m/z): 424

Example 1

Ethylene polymerization was carried out using a batch polymerization reactor as follows. In a 200 mL stainless steel reactor sufficiently dried and purged with nitrogen, 102 mL of cyclohexane and 2.98 mL of 67.05 mM modified methylaluminoxane-7 (modified MAO-7, Akzo Nobel, 7 wt % Al Isopar solution) toluene solution were added. After heating the reactor to 140° C., 0.858 mL of (dichloro)(pentamethylcyclopentadienyl)(2-thiophen-2'-yl)phenoxy)titanium(IV) (1.16 mM toluene solution) synthesized in Preparation Example 1 and 0.74 mL of 4.07 mM triphenylmethyliniumtetrakis(pentafluorophenyl)borate (99%, Boulder Scientific) toluene solution were added sequentially. Ethylene was supplied until its pressure inside the reactor reached 30 kg/cm$^2$. Polymerization was carried out while continuously supplying ethylene. The temperature reached the highest 165° C. 3 minutes after the reaction started. 10 minutes later, 10 mL of ethanol including 10 vol % aqueous hydrochloric acid solution was added to terminate the polymerization. After stirring for 4 hours in 1,500 mL of ethanol, the reaction product was separated by filtering. The collected reaction product was dried in a vacuum oven of 60° C. for 8 hours. 2.92 g of polymer was obtained. Melt index of the polymer was immeasurable. Gel chromatography analysis yielded a weight average molecular weight (M$_w$) of 406,700 g/mol and a molecular weight distribution (M$_w$/M$_n$) of 1.82.

Example 2

Copolymerization of ethylene and 1-octene was carried out using a batch polymerization reactor as follows. In a 200 mL stainless steel reactor sufficiently dried and purged with nitrogen, 93 mL of cyclohexane, 8 mL of 1-octene and 3.73 mL of 67.05 mM modified MAO-7 (Akzo Nobel, 7 wt % Al Isopar solution) toluene solution were added. After heating the reactor to 142.4° C., 1.19 mL of (dichloro)(pentamethylcyclopentadienyl)(2-thiophen-2'-yl)phenoxy)titanium(IV) (0.84 mM toluene solution) synthesized in Preparation Example 1 and 0.65 mL of 4.65 mM triphenylmethyliniumtetrakis(pentafluorophenyl)borate (99%, Boulder Scientific) toluene solution were added sequentially. Ethylene was supplied until its pressure inside the reactor reached 30 kg/cm$^2$. Polymerization was carried out while continuously supplying ethylene. The temperature reached the highest 169.6° C. 1 minute after the reaction started. 1 minute later, 10 mL of ethanol including 10 vol % aqueous hydrochloric acid solution was added to terminate the polymerization. After stirring for 1 hour in 1,500 mL of ethanol, the reaction product was separated by filtering. The collected reaction product was dried in a vacuum oven of 60° C. for 8 hours. 2.32 g of polymer was obtained. Melting point of the polymer was 111.0° C. Melt index was 0.0366 and density was 0.9134 g/cc. Gel chromatography analysis yielded a weight average molecular weight ($M_w$) of 204,200 g/mol and a molecular weight distribution ($M_w/M_n$) of 3.07. 1-Octene content was 9.4% by weight.

Example 3

Ethylene polymerization was carried out using a batch polymerization reactor as follows. In a 200 mL stainless steel reactor sufficiently dried and purged with nitrogen, 97 mL of cyclohexane and 2.98 mL of 67.05 mM modified MAO-7 (Akzo Nobel, 7 wt % Al Isopar solution) toluene solution were added. After heating the reactor to 140° C., 0.848 mL of (dichloro)(pentamethylcyclopentadienyl)(2-(pyridin-2-yl)phenoxy)titanium(IV) (1.18 mM toluene solution) synthesized in Preparation Example 2 and 0.55 mL of 5.42 mM triphenylmethyliniumtetrakis(pentafluorophenyl)borate (99%, Boulder Scientific) toluene solution were added sequentially. Ethylene was supplied until its pressure inside the reactor reached 30 kg/cm². Polymerization was carried out while continuously supplying ethylene. The temperature reached the highest 166.0° C. 3 minutes after the reaction started. 10 minutes later, 10 mL of ethanol including 10 vol % aqueous hydrochloric acid solution was added to terminate the polymerization. After stirring for 4 hours in 1,500 mL of ethanol, the reaction product was separated by filtering. The collected reaction product was dried in a vacuum oven of 60° C. for 8 hours. 4.55 g of polymer was obtained. Melt index of the polymer was immeasurable. Gel chromatography analysis yielded a weight average molecular weight ($M_w$) of 441,300 g/mol and a molecular weight distribution ($M_w/M_n$) of 2.42.

Example 4

Copolymerization of ethylene and 1-octene was carried out using a batch polymerization reactor as follows. In a 200 mL stainless steel reactor sufficiently dried and purged with nitrogen, 88 mL of cyclohexane, 8 mL of 1-octene and 3.73 mL of 67.05 mM modified MAO-7 (Akzo Nobel, 7 wt % Al Isopar solution) toluene solution were added. After heating the reactor to 142° C., 0.848 mL of (dichloro)(pentamethylcyclopentadienyl)(2-(pyridin-2-yl)phenoxy)titanium(IV) (1.18 mM toluene solution) synthesized in Preparation Example 2 and 0.553 mL of 5.42 mM triphenylmethyliniumtetrakis(pentafluorophenyl)borate (99%, Boulder Scientific) toluene solution were added sequentially. Ethylene was supplied until its pressure inside the reactor reached 30 kg/cm². Polymerization was carried out while continuously supplying ethylene. The temperature reached the highest 172.0° C. 1 minute after the reaction started. 1 minute later, 10 mL of ethanol including 10 vol % aqueous hydrochloric acid solution was added to terminate the polymerization. After stirring for 1 hour in 1,500 mL of ethanol, the reaction product was separated by filtering. The collected reaction product was dried in a vacuum oven of 60° C. for 8 hours. 4.12 g of polymer was obtained. Melting point of the polymer was 105.2° C. Melt index was 0.326 and density was 0.9082 g/cc. Gel chromatography analysis yielded a weight average molecular weight ($M_w$) of 122,700 g/mol and a molecular weight distribution ($M_w/M_n$) of 2.11. 1-Octene content was 11.7% by weight.

Description was made in detail with reference to example embodiments. However, it will be appreciated by those skilled in the art that changes may be made in these embodiments without departing from the principles and spirit of the invention, the scope of which is defined in the accompanying claims and their equivalents.

The invention claimed is:

1. A transition metal complex represented by the following Chemical Formula I, which has, around a group IV transition metal, a cyclopentadiene derivative and at least one aryl oxide ligand with a heterocyclic aryl derivative substituted at the ortho-position thereof, with no crosslinkage between the cyclopentadiene derivative and the at least one aryl oxide ligand:

[Chemical Formula 1]

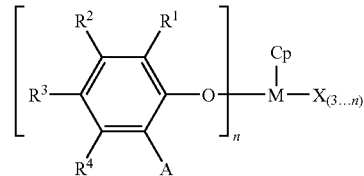

wherein

M is a group IV transition metal in the periodic table;

Cp is a cyclopentadienyl ring or a fused ring including a cyclopentadienyl ring, which is η⁵-bonded to the central metal M, wherein the cyclopentadienyl ring or cyclopentadienyl fused ring may be further substituted with (C1-C20) alkyl, (C6-C30) aryl, (C2-C20) alkenyl or (C6-C30) aryl (C1-C20) alkyl;

A is a substituent

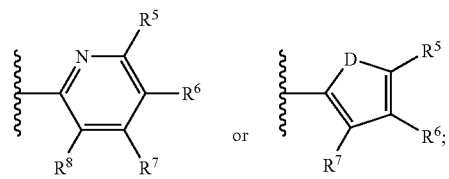

$R^1, R^2, R^3, R^4, R^5, R^6, R^7$ and $R^8$ are, independently of each other, hydrogen, (C1-C20) alkyl, (C3-C20) cycloalkyl, (C1-C20) alkyl-substituted or (C6-C30) aryl-substituted silyl, (C6-C30) aryl, (C6-C30) aryl (C1-C10) alkyl, (C1-C20) alkoxy, (C1-C20) alkyl-substituted or (C6-C20) aryl-substituted siloxy, (C1-C20) alkyl-substituted or (C6-C30) aryl-substituted amino, (C1-C20) alkyl-substituted or (C6-C30) aryl-substituted phosphino, (C1-C20) alkyl-substituted mercapto or nitro, wherein the alkyl, aryl or alkoxy group of said $R^1$ to $R^8$ may be further substituted with halogen or may form a fused ring together with a neighboring substituent;

D is N—$R^9$, oxygen or sulfur;

$R^9$ is linear or branched (C1-C20) alkyl, (C6-C30) aryl, (C1-C20) alkyl-substituted or (C6-C30) aryl-substituted silyl;

n is an integer 1 or 2; and

X is, independently of each other, halogen, (C1-C20) alkyl, (C3-C20) cycloalkyl, (C6-C30) aryl (C1-C20) alkyl, (C1-C20) alkoxy, (C3-C20) alkylsiloxy, (C1-C20) alkyl-substituted or (C6-C30) aryl-substituted amino, (C1-C20) alkyl-substituted or (C6-C30) aryl-substituted phosphino or (C1-C20) alkyl-substituted mercapto.

2. The transition metal complex according to claim 1, wherein said M is titanium.

3. The transition metal complex according to claim 1, wherein said Cp is cyclopentadienyl or pentamethylcyclopentadienyl.

4. The transition metal complex according to claim 1, wherein said $R^1$, $R^2$, $R^3$, $R^4$, $R^5$, $R^6$, $R^7$ and $R^8$ are, independently of each other, selected from hydrogen, methyl and isopropyl.

5. The transition metal complex according to claim 1, wherein said X is, independently of each other, selected from chlorine, methyl, methoxy, isopropoxy and dimethylamino.

6. The transition metal complex according to claim 1, wherein said n is 2.

7. A transition metal catalyst composition for the preparation of an ethylene homopolymer or a copolymer of ethylene and α-olefin comprising:
the transition metal complex according to any of claims 1 to 6; and
an alkylaluminoxane or organoaluminum cocatalyst, a boron compound cocatalyst or a mixture thereof.

8. The transition metal catalyst composition for the preparation of an ethylene homopolymer or a copolymer of ethylene and α-olefin according to claim 7, wherein the alkylaluminoxane cocatalyst is methylaluminoxane.

9. The transition metal catalyst composition for the preparation of an ethylene homopolymer or a copolymer of ethylene and α-olefin according to claim 7, wherein a molar ratio of transition metal M:aluminum atom is 1:50 to 1:5,000.

10. The transition metal catalyst composition for the preparation of an ethylene homopolymer or a copolymer of ethylene and α-olefin according to claim 7, wherein the boron compound cocatalyst is selected from N,N-dimethylanilinium tetrakis(pentafluorophenyl)borate or triphenylmethylinium tetrakis(pentafluorophenyl)borate.

11. The transition metal catalyst composition for the preparation of an ethylene homopolymer or a copolymer of ethylene and α-olefin according to claim 7, wherein a molar ratio of transition metal M:boron atom:aluminum atom is 1:0.5-5: 25-500.

12. The transition metal catalyst composition for the preparation of an ethylene homopolymer or a copolymer of ethylene and α-olefin according to claim 7, wherein the aluminoxane or organoaluminum cocatalyst is selected from methylaluminoxane, triethylaluminum, triisobutylaluminum or a mixture thereof.

13. A method for the preparation of an ethylene homopolymer or a copolymer of ethylene and α-olefin using the transition metal complex according to claim 1, wherein ethylene is polymerized with at least one comonomer selected from propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene or 1-eicosene, and the ethylene content in the copolymer of ethylene and α-olefin is 60-99% by weight.

14. A method for the preparation of an ethylene homopolymer or a copolymer of ethylene and α-olefin using the transition metal catalyst composition according to claim 7, wherein ethylene is polymerized with at least one comonomer selected from propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene or 1-eicosene, and the ethylene content in the copolymer of ethylene and α-olefin is 60-99% by weight.

15. The method for the preparation of an ethylene homopolymer or a copolymer of ethylene and α-olefin according to claim 13, wherein a pressure of the ethylene monomer in a reactor is 8-150 atm and a polymerization temperature is 80-250° C.

16. The method for the preparation of an ethylene homopolymer or a copolymer of ethylene and α-olefin according to claim 14, wherein a pressure of the ethylene monomer in a reactor is 8-150 atm and a polymerization temperature is 80-250° C.

* * * * *